(12) United States Patent
Bishop et al.

(10) Patent No.: US 7,076,142 B2
(45) Date of Patent: Jul. 11, 2006

(54) COATED PHOTONIC CRYSTAL FIBERS

(75) Inventors: Timothy E. Bishop, Algonquin, IL (US); Tosko Misev, Naperville, IL (US)

(73) Assignee: DSM IP Assets B.V., Heerlen (NL)

( * ) Notice: Subject to any disclaimer, the term of this patent is extended or adjusted under 35 U.S.C. 154(b) by 84 days.

(21) Appl. No.: 10/622,192

(22) Filed: Jul. 18, 2003

(65) Prior Publication Data

US 2004/0105643 A1    Jun. 3, 2004

Related U.S. Application Data

(60) Provisional application No. 60/396,570, filed on Jul. 18, 2002.

(51) Int. Cl.
*G02B 6/036* (2006.01)
(52) U.S. Cl. .................... 385/128; 385/114
(58) Field of Classification Search ............. 428/364; 522/71–86; 385/128; 645/430–432
See application file for complete search history.

(56) References Cited

U.S. PATENT DOCUMENTS

| | | | |
|---|---|---|---|
| 4,707,076 A * | 11/1987 | Skutnik et al. ............. 385/145 |
| 5,416,880 A * | 5/1995 | Edwards et al. ............ 385/128 |
| 5,904,983 A | 5/1999 | Chan et al. |
| 6,243,522 B1 | 6/2001 | Allan et al. |
| 6,309,747 B1 * | 10/2001 | Suwa et al. ................. 428/378 |
| 6,323,255 B1 * | 11/2001 | Snowwhite ................. 522/120 |
| 6,334,017 B1 | 12/2001 | West |
| 6,334,019 B1 | 12/2001 | Birks et al. |
| 6,377,724 B1 | 4/2002 | Bookbinder et al. |
| 6,775,450 B1 * | 8/2004 | Maroney et al. ............ 385/126 |
| 6,810,187 B1 * | 10/2004 | Fabian et al. ............... 385/128 |

FOREIGN PATENT DOCUMENTS

| | | |
|---|---|---|
| EP | 0 735 395 | 10/1996 |
| EP | 1 118 887 | 7/2001 |
| WO | WO 01 37008 | 5/2001 |
| WO | WO 02 10817 | 2/2002 |

OTHER PUBLICATIONS

Temelkuran et al., "Wavelength-Scalable Hollow Optical Fibres with Large Ptotonic Bandgaps for CO2 Laser Transmission", Nature, vol. 420, Dec. 12, 2002, pp. 650-653 and Supplemental Information (5 pages).
Hecht et al., "Holes in Photonic Crystal Fibers Open New Possibilities", WDM Solutions, Jan. 2003, pp. 24-27.
Chemical Abstracts + Indexes, American Chemical Society, Columbus, US, vol. 110, No. 10, May 16, 1989, XP000057615, ISSN: 0009-2258.
Chemical Abstracts + Indexes, American Chemical Society, Columbus, US, vol. 109, No. 20, Nov. 20, 1988, XP000155443, ISSN: 0009-2258.
Chemical Abstracts + Indexes, American Chemical Society, Columbus, US, vol. 112, No. 2, Jan. 8, 1990, XP000154210, ISSN: 0009-2258.
International Search Report from PCT/NL03/05535 issued Nov. 25, 2003.

* cited by examiner

*Primary Examiner*—John D. Lee
*Assistant Examiner*—Jerry T. Rahill
(74) *Attorney, Agent, or Firm*—Mayer, Brown, Rowe & Maw LLP

(57) ABSTRACT

The present invention relates to coated photonic crystal fibers including a photonic crystal fiber and a protective coating surrounding the photonic crystal fiber. The coating is obtained by curing a resin composition, which may include a urethane (meth)acrylate oligomer. The present invention also relates to a coated photonic crystal fiber including a photonic crystal fiber and a protective coating having a refractive index below 1.45.

25 Claims, No Drawings

COATED PHOTONIC CRYSTAL FIBERS

CROSS REFERENCE TO RELATED APPLICATIONS

The present application claims the benefit of U.S. provisional application 60/396,570, which was filed on Jul. 18, 2002, and which is hereby incorporated in its entirety by reference.

FIELD OF THE INVENTION

The present invention relates to coated photonic crystal fibers.

BACKGROUND

Recently the optical fiber art has seen the development of so-called photonic crystal fibers. These fibers rely on Bragg reflections to propagate light signals and are less sensitive to microbending than conventional optical fibers. Such photonic fibers have been the subject of several recent US Patents. See, for instance, U.S. Pat. Nos. 6,243,522 B1; 6,301,420 B1; and 6,334,017 B1. Little or no attention has been paid, however, to providing coatings that suitably protect the photonic crystal fibers' strength and integrity while preserving advantages that photonic crystal fibers provide, such as the resistance to microbending.

SUMMARY OF THE INVENTION

The present invention provides coated photonic crystal fibers.

In one embodiment the present invention provides a coated photonic crystal fiber comprising:
(i) a photonic crystal fiber; and
(ii) at least one coating obtained by curing a resin composition.

Another example of an embodiment provided by the present invention is a coated photonic crystal fiber comprising:
(i) a photonic crystal fiber; and
(ii) at least one coating having a refractive index below 1.45.

DESCRIPTION OF THE INVENTION

The present invention relates to coated photonic crystal fibers. Such photonic crystal fibers are disclosed in, for instance, U.S. Pat. No. 6,243,522 B1, U.S. Pat. No. 6,301,420 B1, and U.S. Pat. No. 6,334,017 B1, which three patents are hereby incorporated in their entirety by reference. Commercial suppliers of photonic crystal fibers include Omniguide (US), Crystal Fibre (Denmark), and BlazePhotonics (UK).

According to the present invention, the photonic crystal fibers have at least one coating. Preferred coatings include those that are obtained by curing a resin composition and/or that have a refractive index below 1.45, such as below 1.43, below 1.40, below 1.37, or below 1.35.

As noted, the present at least one coating may be obtained by curing a coating resin composition, preferably by exposing a curable resin composition to heat or radiation. Preferably, the resin composition is curable by at least radiation, for instance by electron beam radiation or ultraviolet radiation.

Preferably, the photonic crystal fiber will have at least one coating having one or more, more preferably three or more, most preferably all five, of the following properties:
(a) an elongation to break of at least 25% (e.g. >50%, >75%, or >100%);
(b) a secant modulus below 100 MPa (e.g. <75 MPa, <50 MPa, <10 MPa, or <2.5 MPa);
(c) an adhesion to glass at 50% RH of at least 0.2 N (e.g. >0.30 N, >0.40 N, or >0.50 N);
(d) an adhesion to glass at 95% RH of at least 0.02 N (e.g. >0.05 N, >0.15 N, or >0.35 N); and
(e) a water sensitivity of less than 10 wt % (e.g. <7 wt %, <4 wt %, <2 wt %, or <1 wt %).

In one embodiment, it is preferred that the optical fiber is surrounded by at least two coatings obtained by curing a resin composition, for instance by a soft primary coating layer of a flexible resin (low modulus and low Tg) which is coated directly onto the cladding, and a secondary coating layer of a rigid resin (higher modulus and higher Tg) which is provided over the primary coating layer. For identification purposes, it may be beneficial to further provide an ink coating over the secondary coating, or to add a colorant to the secondary coating itself prior to curing.

Preferred primary coatings include those having one or more of the following properties:
(i) an elongation to break of at least 75%, for instance at least 100% or at least 150%, and generally below 400%;
(ii) a glass transition temperature (Tg) of at most 10° C., for instance less than 0° C., less than −10° C., less than −20° C., or less than −40° C., and generally above −120° C.; and
(iii) a secant modulus of at most 10 MPa, for instance less than 5 MPa, less than 2 MPa, or less than 1.5 MPa, and generally above 0.1 MPa.

Preferred secondary coatings include those having one or more of the following properties:
(i) an elongation to break of at most 60%, for instance at most 40%, and generally above 3%;
(ii) a glass transition temperature (Tg) of at least 30° C., for instance at least 40° C., at least 50° C., at least 70° C., or at least 90° C., and generally below 200° C.; and
(iii) a secant modulus of at least 100 MPa, for instance at least 300 MPa, at least 500 MPa, or at least 750 MPa, and generally below 2000 MPa.

In one embodiment, the resin composition comprises an oligomer and, optionally, one or more diluents and photoinitiators. Preferred oligomers include oligomers comprising at least one ethylenically unsaturated group, for instance oligomers comprising one or more (meth)acrylate groups.

In one embodiment, the composition comprises a urethane (meth)acrylate oligomer, i.e. an oligomer comprising a (meth)acrylate group, a urethane group, and a backbone. The backbone may be a polyol residue, and the oligomer may be obtained by reacting one or more polyols with one or more polyisocyanates (e.g. diisocyanates) and one or more hydroxy-functional alkyl acrylate. However, urethane-free ethylenically unsaturated oligomers may also be used.

Examples of suitable polyols are polyether polyols, polyester polyols, polycarbonate polyols, polycaprolactone polyols, acrylic polyols, fluorinated polyols, and the like. These polyols may be used either individually or in combinations of two or more. There are no specific limitations to the manner of polymerization of the structural units in these polyols. Any of random polymerization, block polymerization, or graft polymerization is, for instance, acceptable.

Given as examples of the polyether polyols are polyethylene glycol, polypropylene glycol, polypropylene glycolethyleneglycol copolymer, polytetramethylene glycol, polyhexamethylene glycol, polyheptamethylene glycol, polydecamethylene glycol, and polyether diols obtained by ring-opening copolymerization of two or more ion-polymerizable cyclic compounds. Here, given as examples of the ion-polymerizable cyclic compounds are cyclic ethers such as ethylene oxide, isobutene oxide, tetrahydrofuran, 2-methyltetrahydrofuran, 3-methyltetrahydrofuran, dioxane, trioxane, tetraoxane, cyclohexene oxide, styrene oxide, epichlorohydrin, isoprene monoxide, vinyl oxetane, vinyl tetrahydrofuran, vinyl cyclohexene oxide, phenyl glycidyl ether, butyl glycidyl ether, and glycidyl benzoate. Specific examples of combinations of two or more ion-polymerizable cyclic compounds include combinations for producing a binary copolymer such as tetrahydrofuran and 2-methyltetrahydrofuran, tetrahydrofuran and 3-methyltetrahydrofuran, and tetrahydrofuran and ethylene oxide; and combinations for producing a ternary copolymer such as a combination of tetrahydrofuran, 2-methyltetrahydrofuran, and ethylene oxide, a combination of tetrahydrofuran, butene-1-oxide, and ethylene oxide, and the like. The ring-opening copolymers of these ion-polymerizable cyclic compounds may be either random copolymers or block copolymers. Included in these polyether polyols are products commercially available under the trademarks, for example, PTMG1000, PTMG2000 (manufactured by Mitsubishi Chemical Corp.), PEG#1000 (manufactured by Nippon Oil and Fats Co., Ltd.), PTG650 (SN), PTG1000 (SN), PTG2000 (SN), PTG3000, PTGL1000, PTGL2000 (manufactured by Hodogaya Chemical Co., Ltd.), PEG400, PEG600, PEG1000, PEG1500, PEG2000, PEG4000, PEG6000 (manufactured by Daiichi Kogyo Seiyaku Co., Ltd.), Acclaim 4200 and Acclaim 4200N (commercially available from Lyondell), and Pluronics (by BASF).

Polyester diols obtained by reacting a polyhydric alcohol and a polybasic acid are given as examples of the polyester polyols. As examples of the polyhydric alcohol, ethylene glycol, polyethylene glycol, tetramethylene glycol, polytetramethylene glycol, 1,6-hexanediol, 3-methyl-1,5-pentanediol, 1,9-nonanediol, 2-methyl-1,8-octanediol, and the like can be given. As examples of the polybasic acid, phthalic acid, dimer acid, isophthalic acid, terephthalic acid, maleic acid, fumaric acid, adipic acid, sebasic acid, and the like can be given. These polyester polyol compounds are commercially available under the trademarks such as MPD/IPA500, MPD/IPA1000, MPD/IPA2000, MPD/TPA500, MPD/TPA1000, MPD/TPA2000, Kurapol A-1010, A-2010, PNA-2000, PNOA-1010, and PNOA-2010 (manufactured by Kuraray Co., Ltd.).

As examples of the polycarbonate polyols, polycarbonate of polytetrahydrofuran, poly(hexanediol carbonate), poly(nonanediol carbonate), poly(3-methyl-1,5-pentamethylene carbonate), and the like can be given. As commercially available products of these polycarbonate polyols, DN-980, DN-981 (manufactured by Nippon Polyurethane Industry Co., Ltd.), Priplast 3196, 3190, 2033 (manufactured by Unichema), PNOC-2000, PNOC-1000 (manufactured by Kuraray Co., Ltd.), PLACCEL CD220, CD210, CD208, CD205 (manufactured by Daicel Chemical Industries, Ltd.), PC-THF-CD (manufactured by BASF), and the like can be given.

Polycaprolactone diols obtained by reacting ε-caprolactone and a diol compound are given as examples of the polycaprolactone polyols having a melting point of 0° C. or higher. Here, given as examples of the diol compound are ethylene glycol, polyethylene glycol, polypropylene glycol, polypropylene glycol, tetramethylene glycol, polytetramethylene glycol, 1,2-polybutylene glycol, 1,6-hexanediol, neopentyl glycol, 1,4-cyclohexanedimethanol, 1,4-butanediol, and the like. Commercially available products of these polycaprolactone polyols include PLACCEL 240, 230, 230ST, 220, 220ST, 220NP1, 212, 210, 220N, 210N, L230AL, L220AL, L220PL, L220PM, L212AL (all manufactured by Daicel Chemical Industries, Ltd.), Rauccarb 107 (by Enichem), and the like.

Examples of fluorinated polyols are disclosed in, for instance, U.S. Pat. No. 6,391,459, which is hereby incorporated in its entirety by reference. Examples of oligomers having an acrylic backbone are disclosed in, for instance, U.S. Pat. No. 6,309,747, which is hereby incorporated in its entirety by reference.

Examples of suitable polyisocyanates include, for instance, aromatic polyisocyanates such as m-phenylene diisocyanate, p-phenylene diisocyanate, 4,4'-diphenyl diisocyanate, 1,5-naphthalene diisocyanate, 4,4'-diphenylmethane diisocyanate, 2,4- or 2,6-tolylene diisocyanate, 4,4'-toluidine diisocyanate, 4,4'-diphenyl ether diisocyanate, and the like; and polyisocyanates such as triphenylmethane-4,4',4''-triisocyanate, 1,3,5-triisocyanatebenzene, 2,4,6-triisocyanatetoluene, 4,4'-diphenylmethane-2,2',5,5'-tetraisocyanate, and the like. Examples of aromatic aliphatic polyisocyanate include diisocyanates such as 1,3- of 1,4-xylylene diisocyanate or a mixture thereof, 1,3- or 1,4-bis(1-isocyanate-1-methylethyl)benzene or mixtures thereof, and the like; and polyisocyanates such as 1,3,5-triisocyanatemethylbenzene, and the like. Examples of alicyclic polyisocyanates include 1,3-cyclopentene diisocyanate, 1,4-cyclohexane diisocyanate, 1,3-cyclohexane diisocyanate, 3-isocyanatemethyl-3,5,5-trimethylcyclohexyl isocyanate (isophorone diisocyanate), 4,4'-methylenebis(cyclohexyl isocyanate), methyl-2,4-cyclohexane diisocyanate, methyl-2,6-cyclohexane diisocyanate, 1,3- or 1,4-bis(isocyanatemethyl)cyclohexane, and the like; and polyisocyanates such as 1,3,5-triisocyanatecyclohexane, 1,3,5-trimethylisocyanatecyclohexane, 2-(3-isocyanatepropyl)-2,5-di(isocyanatemethyl)-bicyclo(2.2.1)heptane, 2-(3-isocyanatepropyl)-2,6-di(isocyanatemethyl)-bicyclo(2.2.1)heptane, 3-(3-isocyanatepropyl)-2,5-di(isocyanatemethyl)-bicyclo(2.2.1)heptane, 5-(2-isocyanateethyl)-2-isocyanatemethyl-3-(3-isocyanatepropyl)-bicyclo(2.2.1)heptane, 6-(2-isocyanateethyl)-2-isocyanatemethyl-3-(3-isocyanatepropyl)-bicyclo(2.2.1)heptane, 5-(2-isocyanateethyl)-2-isocyanatemethyl-2-(3-isocyanatepropyl)-bicyclo(2.2.1)heptane, 6-(2-isocyanateethyl)-2-isocyanatemethyl)-2-(3-isocyanatepropyl)-bicyclo(2.2.1)heptane, and the like. Examples of aliphatic polyisocyanates include trimethylene diisocyanate, tetramethylene diisocyanate, hexamethylene diisocyanate, pentamethylene diisocyanate, 1,2-propylene diisocyanate, 1,2-butylene diisocyanate, 2,3-butylene diisocyanate, 1,3-butylene diisocyanate, 2,4,4- or 2,2,4-trimethylhexamethylene diisocyanate, 2,6-diisocyanatemethylcaproate, and the like; and polyisocyanates such as lysine ester triisocyanate, 1,4,8-triisocyanateoctane, 1,6,11-triisocyanateundecane, 1,8-diisocyanate-4-isocyanatemethyloctane, 1,3,6-triisocyanatehexane, 2,5,7-trimethyl-1,8-isocyanate-5-isocyanatemethyloctane, and the like.

Examples of suitable hydroxy-functional (meth)acrylates include, for instance, 2-hydroxyethyl (meth)acrylate, 2-hydroxypropyl (meth)acrylate, 2-hydroxybutyl (meth)acrylate, 4-hydroxybutyl (meth)acrylate, pentanediol mono(meth)acrylate, 2-hydroxy-3-phenyloxypropyl (meth)acrylate, 2-hydroxyalkyl(meth)acryloyl phosphate, 4-hydroxycyclohexyl (meth)acrylate, cyclohexanedimethanol mono(meth)

acrylate, neopentyl glycol mono(meth)acrylate, trimethylolpropane di(meth)acrylate, pentaerythritol tri(meth)acrylate, and the like. In addition, compounds which are obtainable by an addition reaction of a glycidyl group-containing compound and a (meth)acrylic acid, such as alkyl glycidyl ether and glycidyl (meth)acrylate, may be used.

The ratio of polyol, di- or polyisocyanate (as disclosed in WO 00/18696, which is hereby incorporated in its entirety by reference), and hydroxyl group-containing (meth)acrylate used for preparing the urethane (meth)acrylate is generally determined so that about 1.1 to about 3 equivalents of an isocyanate group included in the polyisocyanate and about 0.1 to about 1.5 equivalents of a hydroxyl group included in the hydroxyl group-containing (meth)acrylate are used for one equivalent of the hydroxyl group included in the polyol.

In the reaction of these three components, an urethanization catalyst such as copper naphthenate, cobalt naphthenate, zinc naphthenate, di-n-butyl tin dilaurate, triethylamine, and triethylenediamine, 2-methyltriethyleneamine, is usually used in an amount from about 0.01 to about 1 wt % of the total amount of the reactant. The reaction may be carried out at a temperature from about 10 to about 90° C., and preferably from about 30 to about 80° C.

Preferred oligomers include those having a number average molecular weight of at least 500 g/mol. For comparatively soft coatings (e.g. primary coatings), it is generally preferred that the composition comprises an oligomer with a molecular weight of at least 1750 g/mol, for instance at least 2000 g/mol, at least 2500 g/mol, or at least 3500 g/mol. For comparatively hard coatings (e.g. single coatings or, particularly, secondary coatings), it is generally preferred that the composition comprises an oligomer having a molecular weight below 1750 g/mol, for instance below 1500 g/mol, below 1250 g/mol, or below 1000 g/mol.

The present compositions for coating photonic crystal fibers preferably comprise, relative to the total weight of the composition, at least 20% of one or more oligomers, for instance at least 35%, at least 50%, or at least 75%. The compositions generally comprise less than 99 wt %, e.g. less than 95 wt % or less than 90 wt %, of oligomer.

Reactive diluents may optionally be added to the present compositions to further tailor the properties of the compositions, for instance to adjust the viscosity of the composition.

Suitable reactive diluents include polymerizable monomers containing a vinyl group or a (meth)acrylate group. Monofunctional monomers and polyfunctional monomers are included in such polymerizable monomers. Examples of suitable monofunctional monomers include monomers containing a vinyl group, such as N-vinyl pyrrolidone, N-vinyl caprolactam, vinyl imidazole, vinyl pyridine; isobornyl (meth)acrylate, bornyl (meth)acrylate, tricyclodecanyl (meth)acrylate, dicyclopentanyl (meth)acrylate, dicyclopentenyl (meth)acrylate, cyclohexyl (meth)acrylate, benzyl (meth)acrylate, 4-butylcyclohexyl (meth)acrylate, acryloyl morpholine, 2-hydroxyethyl (meth)acrylate, 2-hydroxypropyl (meth)acrylate, 2-hydroxybutyl (meth)acrylate, methyl (meth)acrylate, ethyl (meth)acrylate, propyl (meth)acrylate, isopropyl (meth)acrylate, butyl (meth)acrylate, amyl (meth)acrylate, isobutyl (meth)acrylate, t-butyl (meth)acrylate, pentyl (meth)acrylate, caprolactone acrylate, isoamyl (meth)acrylate, hexyl (meth)acrylate, heptyl (meth)acrylate, octyl (meth)acrylate, isooctyl (meth)acrylate, 2-ethylhexyl (meth)acrylate, nonyl (meth)acrylate, decyl (meth)acrylate, isodecyl (meth)acrylate, undecyl (meth)acrylate, dodecyl (meth)acrylate, lauryl (meth)acrylate, stearyl (meth)acrylate, isostearyl (meth)acrylate, tetrahydrofurfuryl (meth)acrylate, butoxyethyl (meth)acrylate, ethoxydiethylene glycol (meth)acrylate, benzyl (meth)acrylate, phenoxyethyl (meth)acrylate, polyethylene glycol mono(meth)acrylate, polypropylene glycol mono(meth)acrylate, methoxyethylene glycol (meth)acrylate, ethoxyethyl (meth)acrylate, methoxypolyethylene glycol (meth)acrylate, methoxypolypropylene glycol (meth)acrylate, diacetone (meth)acrylamide, isobutoxymethyl (meth)acrylamide, N,N-dimethyl (meth)acrylamide, t-octyl (meth)acrylamide, dimethylaminoethyl (meth)acrylate, diethylaminoethyl (meth)acrylate, 7-amino-3,7-dimethyloctyl (meth)acrylate, N,N-diethyl (meth)acrylamide, N,N-dimethylaminopropyl (meth)acrylamide, hydroxybutyl vinyl ether, lauryl vinyl ether, cetyl vinyl ether, 2-ethylhexyl vinyl ether; and compounds represented by the following formula (2)

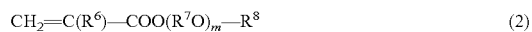

$$CH_2=C(R^6)-COO(R^7O)_m-R^8 \qquad (2)$$

wherein $R^6$ is a hydrogen atom or a methyl group; $R^7$ is an alkylene group containing 2 to 8, preferably 2 to 5 carbon atoms; and m is an integer from 0 to 12, and preferably from 1 to 8; $R^8$ is a hydrogen atom or an alkyl group containing 1 to 12, preferably 1 to 9, carbon atoms; or, $R^8$ is a tetrahydrofuran group-comprising alkyl group with 4–20 carbon atoms, optionally substituted with alkyl groups with 1–2 carbon atoms; or $R^8$ is a dioxane group-comprising alkyl group with 4–20 carbon atoms, optionally substituted with methyl groups; or $R^8$ is an aromatic group, optionally substituted with $C_1$–$C_{12}$ alkyl group, preferably a $C_8$–$C_9$ alkyl group, and alkoxylated aliphatic monofunctional monomers, such as ethoxylated isodecyl (meth)acrylate, ethoxylated lauryl (meth)acrylate, and the like.

Examples of the polyfunctional monomers include monomers containing (meth)acryloyl group such as trimethylolpropane tri(meth)acrylate, pentaerythritol (meth)acrylate, ethylene glycol di(meth)acrylate, tetraethylene glycol di(meth)acrylate, polyethylene glycol di(meth)acrylate, 1,4-butanediol di(meth)acrylate, 1,6-hexanediol di(meth)acrylate, neopentyl glycol di(meth)acrylate, trimethylolpropanetrioxyethyl (meth)acrylate, tris(2-hydroxyethyl) isocyanurate tri(meth)acrylate, tris(2-hydroxyethyl) isocyanurate di(meth)acrylate, tricyclodecane diyl dimethyl di(meth)acrylate, and di(meth)acrylate of a diol which is an ethylene oxide or propylene oxide adduct to bisphenol A, di(meth)acrylate of a diol which is an ethylene oxide or propylene oxide adduct to hydrogenated bisphenol A, epoxy (meth)acrylate which is a (meth)acrylate adduct to bisphenol A of diglycidyl ether, diacrylate of polyoxyalkylated bisphenol A, and triethylene glycol divinyl ether, adduct of hydroxyethyl acrylate, isophorone diisocyanate and hydroxyethyl acrylate (HIH), adduct of hydroxyethyl acrylate, toluene diisocyanate and hydroxyethyl acrylate (HTH), and amide ester acrylate.

Preferred reactive diluents include alkoxylated alkyl substituted phenol acrylates, such as ethoxylated nonyl phenol acrylate, propoxylated nonyl phenol acrylate; vinyl monomers such as vinyl caprolactam; isodecyl acrylate; and alkoxylated bisphenol A diacrylate such as ethoxylated bisphenol A diacrylate. In one embodiment, it is preferred to include one or more alkoxylated aliphatic polyacrylates, for instance an alkoxylated aliphatic diacrylate such as alkoxylated (e.g. propoxylated) neopentyl glycol diacrylate. In another embodiment, it is preferred to include one or more diluents comprising one or more aromatic rings.

The present compositions comprise generally less than 75 wt %, relative to the total weight of the composition, of diluent, for instance less than 65 wt % or less than 50 wt %, or less than 25 wt %.

Suitable photoinitiators include free radical photoinitiators. Free-radical photoinitiators are generally divided into two classes according to the process by which the initiating radicals are formed. Compounds that undergo unimolecular bond cleavage upon irradiation are termed Type I or homolytic photoinitiators. If the excited state photoinitiator interacts with a second molecule (a coinitiator) to generate radicals in a bimolecular reaction, the initiating system is termed a Type II photoinitiator. In general, the two main reaction pathways for Type II photoinitiators are hydrogen abstraction by the excited initiator or photoinduced electron transfer, followed by fragmentation. Examples of suitable free-radical photoinitiators are disclosed in WO 00/18696 which is incorporated herein in its entirety by reference. In one embodiment, the coating compositions comprise at least one photoinitiator having a phosphorous, sulfur or nitrogen atom. In another embodiment, the coating compositions comprise at least a combination of a photoinitiator containing a phosphorous atom and a photoinitiator containing a sulfur atom. In another embodiment, the compositions comprise at least one oligomeric or polymeric photoinitiators.

The present compositions generally comprise less than 10 wt %, relative to the total weight of the composition, of photoinitiator, for instance less than 8 wt %, less than 6 wt %, or less than 4 wt %.

In addition to the above-described components, various additives such as antioxidants, UV absorbers, light stabilizers, silane coupling agents (e.g. mercaptofunctional silane coupling agents in an amount of 0.25–10 wt %, e.g. 0.5–5 wt % or about 1 wt %), coating surface improvers, heat polymerization inhibitors, epoxy-functional components, leveling agents, surfactants, colorants, preservatives, plasticizers, lubricants, solvents, fillers, aging preventives, and wettability improvers can be used in the liquid curable resin composition of the present invention, as required. If the composition comprises epoxy-functional components, it is often preferred to further include one or more cationic photoinitiators (e.g. one or more onium salts).

The compositions for coating the photonic crystal fibers preferably have a viscosity below 15,000 cps at 25° C., for instance below 10,000 cps, below 8,000 cps, or below 6,000 cps. The viscosity will generally be at least 500 cps at 25° C., for instance at least 1,000 cps, at least 2,000 cps, or at least 3,000 cps.

The coated and photonic fibers may be used in a ribbon comprising a plurality of said fibers, generally in a parallel arrangement. The plurality of fibers is further coated with one or more matrix materials in order to obtain a ribbon. The present invention therefore further relates to a ribbon comprising a plurality of coated photonic crystal fibers, generally in a parallel arrangement.

EXAMPLES

The following examples are given as particular embodiments of the invention and to demonstrate the practice and advantages thereof. The examples are given by way of illustration and are not intended to limit the specification or claims.

Example 1

Primary Coating

A composition was prepared by mixing the ingredients listed in Table 1. The composition was subsequently cured with ultraviolet radiation and its physical properties were determined (also listed in Table 1).

TABLE 1

Primary Coating

| Ingredient | Amount (wt %) |
|---|---|
| HEA-TDI-PTGL2000-TDI-PTGL2000-TDI-HEA[1] | 49.9 |
| Ethoxylated nonylphenol acrylate | 20.4 |
| Lauryl acrylate | 7.0 |
| Isobornyl acrylate | 13.7 |
| Vinylcaprolactam | 6.0 |
| gamma-mercaptopropyltrimethoxysilane | 1.0 |
| Lucirin TPO | 1.5 |
| Irganox 1035 | 0.3 |
| Diethylamine | 0.1 |
| Dibutyltin dilaurate | 0.04 |
| Ionol (stabilizer) | 0.012 |
| Phenothiazine | 0.004 |
| Physical Properties | |
| Adhesion to glass, 50% R.H. (N × $10^{-2}$) | 64 |
| Adhesion to glass, 95% R.H. (N × $10^{-2}$) | 55 |
| Elongation to break (%) | 105 |
| Secant Modulus (MPa) | 1.3 |
| Tensile Strength (MPa) | 0.8 |
| Refractive Index | 1.57 |
| Tg (tan δ), ° C. | −20 |
| Water sensitivity (weight change, %) | 0.0 |

[1]HEA = hydroxyethyl acrylate residue.
TDI = toluene diisocyanate residue.
PTGL2000 = methyl-substituted polytetrahydrofuran (Mw about 2000 g/mol) residue.

Example 2

Secondary Coating

A composition was prepared by mixing the ingredients listed in Table 2. The composition was subsequently cured with ultraviolet radiation and its physical properties were determined (also listed in Table 2).

TABLE 2

Secondary Coating

| Ingredient | Amount (wt %) |
|---|---|
| HEA-TDI-PTHF650-TDI-HEA[1] | 40.6 |
| Bisphenol A epoxy diacrylate | 30.2 |
| Isobornyl acrylate | 10.4 |
| Hexanediol diacrylate | 6.3 |
| Phenoxyethyl acrylate | 9.4 |
| Lucirin Low AV | 2.1 |
| Tinuvin 292 | 0.5 |
| Irganox 245 | 0.5 |
| Physical Properties | |
| Elongation to break (%) | 23 |
| Secant Modulus (MPa) | 725 |
| Tensile Strength (MPa) | 30 |
| Refractive Index | 1.54 |
| Tg (tan δ), ° C. | 60 |

[1]HEA = hydroxyethyl acrylate residue.
TDI = toluene diisocyanate residue.
PTHF650 = polytetrahydrofuran (Mw about 650 g/mol) residue.

Example 3

Primary Coating

A composition was prepared by mixing the ingredients listed in Table 3. The composition was subsequently cured with ultraviolet radiation and its physical properties were determined (also listed in Table 3).

TABLE 3

Primary Coating

| Ingredient | Amount (wt %) |
| --- | --- |
| HEA-IPDI-PTGL2000-IPDI-PTGL2000-IPDI-HEA[1] | 49.9 |
| Ethoxylated nonylphenol acrylate | 20.4 |
| Lauryl acrylate | 7.0 |
| Isobornyl acrylate | 13.7 |
| Vinylcaprolactam | 6.0 |
| gamma-mercaptopropyltrimethoxysilane | 1.0 |
| Lucirin TPO | 1.5 |
| Irganox 1035 | 0.3 |
| Diethylamine | 0.1 |
| Dibutyltin dilaurate | 0.04 |
| Ionol (stabilizer) | 0.012 |
| Phenothiazine | 0.004 |
| Physical Properties | |
| Adhesion to glass, 50% R.H. (N × $10^{-2}$) | 90 |
| Adhesion to glass, 95% R.H. (N × $10^{-2}$) | 50 |
| Elongation to break (%) | 140 |
| Secant Modulus (MPa) | 1.3 |
| Tensile Strength (MPa) | 0.9 |
| Refractive Index | 1.57 |
| Tg (tan δ), ° C. | −15 |

[1]HEA = hydroxyethyl acrylate residue.
IPDI = isophorone diisocyanate residue.
PTGL2000 = methyl-substituted polytetrahydrofuran (Mw about 2000 g/mol) residue.

Example 4

Secondary Coating

A composition was prepared by mixing the ingredients listed in Table 4. The composition was subsequently cured with ultraviolet radiation and its physical properties were determined (also listed in Table 4).

TABLE 4

Secondary Coating

| Ingredient | Amount (wt %) |
| --- | --- |
| HEA-IPDI-PC-IPDI-HEA[1] | 34.2 |
| Bisphenol A ethoxylate diacrylate | 48 |
| Ethoxylated nonyl phenol acrylate | 4.8 |
| Phenoxyethyl acrylate | 10.2 |
| Irganox 245 | 0.4 |
| Irgacure 184 | 2.4 |
| Physical Properties | |
| Elongation to break (%) | 22 |
| Secant Modulus (MPa) | 470 |
| Tensile Strength (MPa) | 22 |
| Refractive Index | 1.54 |
| Tg (tan δ), ° C. | 43 |

[1]HEA = hydroxyethyl acrylate residue.
IPDI = isophorone diisocyanate residue.
PC = polycarbonate diol (Permanol KM10-1733 from Permuthane, Inc., Ma.) residue.

Example 5

Single Coating

A composition was prepared by mixing the ingredients listed in Table 5. The composition was subsequently cured with ultraviolet radiation and its physical properties were determined (also listed in Table 5).

TABLE 5

Single Coating

| Ingredient | Amount (wt %) |
| --- | --- |
| HEA-IPDI-PTHF650-IPDI-HEA[1] | 75.9 |
| Ethoxy ethoxy ethyl acrylate | 12.4 |
| Trimethylolpropane triacrylate | 9.1 |
| Lucirin TPO | 2 |
| DC-57 silicone additive | 0.1 |
| DC-190 silicone additive | 0.2 |
| Diethyl amine | 0.3 |
| Physical Properties | |
| Elongation to break (%) | 50 |
| Secant Modulus (MPa) | 40 |
| Tensile Strength (MPa) | 12 |
| Refractive Index | 1.54 |
| Tg (tan δ), ° C. | 32 |
| Adhesion to glass, 50% R.H. (N × $10^{-2}$) | 50 |
| Adhesion to glass, 95% R.H. (N × $10^{-2}$) | 5 |
| Water sensitivity (weight change, %) | 2.0 |

[1]HEA = hydroxyethyl acrylate residue.
IPDI = toluene diisocyanate residue.
PTHF650 = polytetrahydrofuran (Mw about 650 g/mol) residue.

Example 6

Single Coating

A composition was prepared by mixing the ingredients listed in Table 4. The composition was subsequently cured with ultraviolet radiation and its physical properties were determined (also listed in Table 6).

TABLE 6

Single Coating

| Ingredient | Amount (wt %) |
| --- | --- |
| HEA-IPDI-FluorolinkE-IPDI-HEA[1] | 80.7 |
| Hexanediol diacrylate | 16 |
| Lucirin TPO | 0.5 |
| Irgacure 184 | 1.5 |
| Irganox 1035 | 0.3 |
| Gamma-mercaptopropyltrimethoxy silane | 1.0 |
| Physical Properties | |
| Elongation to break (%) | 25 |
| Secant Modulus (MPa) | 140 |
| Tensile Strength (MPa) | 10 |
| Viscosity at 25° C. (mPa · s) | 6000 |
| Liquid Refractive Index | 1.40 |

[1]HEA = hydroxyethyl acrylate residue.
IPDI = isophorone diisocyanate residue.
Fluorolink E = fluorinated polyether diol (Fluorolink E from Ausimont) residue.

Test Methods

Tensile Strength, Elongation, and Modulus Test Method

The tensile properties (tensile strength, percent elongation at break, and modulus) of cured samples were determined using an Instron model 4201 universal testing instrument. Samples were prepared for testing by curing a 75-μm film of the material using a Fusion UV processor. Samples were cured at 1.0 J/cm² in a nitrogen atmosphere. Test specimens having a width of 0.5 inches and a length of 5 inches were cut from the film. The exact thickness of each specimen was measured with a micrometer.

For soft coatings (e.g., those with a modulus of less than about 10 MPa), the coating was drawn down and cured on a glass plate and the individual specimens cut from the glass plate with a scalpel. A 2-lb load cell was used in the Instron and modulus was calculated at 2.5% elongation with a least squares fit of the stress-strain plot. Cured films were conditioned at 23±1° C. and 50±5% relative humidity for a minimum of one hour prior to testing.

For harder coatings, the coating was drawn down on a Mylar film and specimens were cut with a Thwing Albert 0.5-inch precision sample cutter. A 20-lb load cell was used in the Instron and modulus was calculated at 2.5% elongation from the secant at that point. Cured films were conditioned at 23±1° C. and 50±5% relative humidity for sixteen hours prior to testing.

For testing specimens, the gage length was 2-inches and the crosshead speed was 1.00 inches/minute. All testing was done at a temperature of 23±1° C. and a relative humidity of 50±5%. All measurements were determined from the average of at least 6 test specimens.

DMA Test Method

Dynamic Mechanical Analysis (DMA) was carried out on the test samples, using an RSA-II instrument manufactured by Rheometric Scientific Inc. A free film specimen (typically about 36 mm long, 12 mm wide, and 0.075 mm thick) was mounted in the grips of the instrument, and the temperature initially brought to 80° C. and held there for about five minutes. During the latter soak period at 80° C., the sample was stretched by about 2.5% of its original length. Also during this time, information about the sample identity, its dimensions, and the specific test method was entered into the software (RSI Orchestrator) residing on the attached personal computer.

All tests were performed at a frequency of 1.0 radians, with the dynamic temperature step method having 2° C. steps, a soak time of 5 to 10 seconds, an initial strain of about 0.001 (ΔL/L), and with autotension and autostrain options activated. The autotension was set to ensure that the sample remained under a tensile force throughout the run, and autostrain was set to allow the strain to be increased as the sample passed through the glass transition and became softer. After the 5 minute soak time, the temperature in the sample oven was reduced in 20° C. steps until the starting temperature, typically −80° C. or −60° C., was reached. The final temperature of the run was entered into the software before starting the run, such that the data for a sample would extend from the glassy region through the transition region and well into the rubbery region.

The run was started and allowed to proceed to completion. After completion of the run, a graph of E', E", and tan delta, all versus temperature, appeared on the computer screen. The data points on each curve were smoothed, using a program in the software. On this plot, three points representing the glass transition were identified: 1) The temperature at which E'=1000 MPa; 2) The temperature at which E'=100 MPa; 3) The temperature of the peak in the tan delta curve. If the tan delta curve contained more than one peak, the temperature of each peak was measured. One additional value obtained from the graph was the minimum value for E' in the rubbery region. This value was reported as the equilibrium modulus, $E_0$.

Measurement of Dry and Wet Adhesion

Determination of dry and wet adhesion was performed using an Instron model 4201 universal testing instrument. A 75-μm film was drawn down on a polished TLC glass plate and cured using a Fusion UV processor. Samples were cured at 1.0 J/cm² in a nitrogen atmosphere.

The samples were conditioned at a temperature of 23±1° C. and a relative humidity of 50±5% for a period of 7 days. After conditioning, eight specimens were cut 6 inches long and 1 inch wide with a scalpel in the direction of the draw down. A thin layer of talc was applied to four of the specimens. The first inch of each sample was peeled back from the glass. The glass was secured to a horizontal support on the Instron with the affixed end of the specimen adjacent to a pulley attached to the support and positioned directly underneath the crosshead. A wire was attached to the peeled-back end of the sample, run along the specimen and then run through the pulley in a direction perpendicular to the specimen. The free end of the wire was clamped in the upper jaw of the Instron, which was then activated. The test was continued until the average force value, in grams force/inch, became relatively constant. The crosshead speed was 10 in/min. Dry adhesion was the average of the four specimens.

The remaining four specimens were then conditioned at 23±1° C. and a relative humidity of 95±5% for 24 hours. A thin layer of a polyethylene/water slurry was applied to the surface of the specimens. Testing was then performed as in the previous paragraph. Wet adhesion was the average of the four specimens.

Water Sensitivity

A layer of the composition was cured to provide a UV cured coating test strip (1.5 inch×1.5 inch×6 mils). The test strip was weighed and placed in a vial containing deionized water, which was subsequently stored for 3 weeks at 23° C. At periodic intervals, e.g. 30 minutes, 1 hour, 2 hours, 3 hours, 6 hours, 1 day, 2 days, 3 days, 7 days, 14 days, and 21 days, the test strip was removed from the vial and gently patted dry with a paper towel and reweighed. The percent water absorption was reported as 100*(weight after immersion−weight before immersion)/(weight before immersion). The peak water absorption was the highest water absorption value reached during the 3-week immersion period. At the end of the 3-week period, the test strip was dried in a 60° C. oven for 1 hour, cooled in a desiccator for 15 minutes, and reweighed. The percent water extractables was reported as 100*(weight before immersion−weight after drying)/(weight before immersion). The water sensitivity was reported as |peak water absorption|+|water extractables|. Three test strips were tested to improve the accuracy of the test.

Refractive Index

The refractive index of the cured compositions was determined with the Becké Line method, which entails matching the refractive index of finely cut strips of the cured composition with immersion liquids of known refraction properties. The test was performed under a microscope at 23° C. and with light having a wavelength of 589 nm.

Viscosity

The viscosity was measured using a Physica MC10 Viscometer. The test samples were examined and if an excessive amount of bubbles was present, steps were taken to remove most of the bubbles. Not all bubbles need to be removed at this stage, because the act of sample loading introduces some bubbles.

The instrument was set up for the conventional Z3 system, which was used. The samples were loaded into a disposable aluminum cup by using the syringe to measure out 17 cc. The sample in the cup was examined and if it contains an excessive amount of bubbles, they were removed by a direct means such as centrifugation, or enough time was allowed to elapse to let the bubbles escape from the bulk of the liquid. Bubbles at the top surface of the liquid are acceptable.

The bob was gently lowered into the liquid in the measuring cup, and the cup and bob were installed in the instrument. The sample temperature was allowed to equilibrate with the temperature of the circulating liquid by waiting five minutes. Then, the rotational speed was set to a desired value which will produce the desired shear rate. The desired value of the shear rate is easily determined by one of ordinary skill in the art from an expected viscosity range of the sample. The shear rate is typically 50–100 sect$^{-1}$.

The instrument panel read out a viscosity value, and if the viscosity value varied only slightly (less than 2% relative variation) for 15 seconds, the measurement was complete. If not, it is possible that the temperature had not yet reached an equilibrium value, or that the material was changing due to shearing. If the latter case, further testing at different shear rates will be needed to define the sample's viscous properties. The results reported are the average viscosity values of three test samples.

Having described specific embodiments of the present invention, it will be understood that many modifications thereof will readily be apparent to those skilled in the art, and it is intended therefore that this invention is limited only by the spirit and scope of the following claims.

What is claimed is:

1. A coated photonic crystal fiber comprising:
   (i) a photonic crystal fiber; and
   (ii) a protective coating surrounding said photonic crystal fiber, wherein said protective coating has the following combination of properties
      (a) an elongation to break of at least 25%;
      (b) a secant modulus below 100 MPa;
      (c) an adhesion to glass at 50% RH of at least 0.2 N;
      (d) an adhesion to glass at 95% RH of at least 0.02 N; and/or
      (e) a water sensitivity of less than 10 wt %.

2. An optical fiber ribbon comprising a plurality of coated photonic crystal fibers according to claim 1.

3. The coated photonic crystal fiber of claim 1, wherein said protective coating has an elongation to break of at least 50%.

4. The coated photonic crystal fiber of claim 1, wherein said protective coating has an elongation to break of at least 100%.

5. The coated photonic crystal fiber of claim 1, wherein said protective coating has a secant modulus below 50 MPa.

6. The coated photonic crystal fiber of claim 1, wherein said protective coating has a secant modulus below 2.5 MPa.

7. The coated photonic crystal fiber of claim 1, wherein said protective coating has an adhesion to glass at 50% RH of at least 0.3 N.

8. The coated photonic crystal fiber of claim 1, wherein said protective coating has an adhesion at 50% RH of at least 0.5 N.

9. The coated photonic crystal fiber of claim 1, wherein said protective coating has an adhesion at 95% RH of at least 0.04 N.

10. The coated photonic crystal fiber of claim 1, wherein said protective coating has an adhesion at 95% RH of at least 0.15 N.

11. The coated photonic crystal fiber of claim 1, wherein said protective coating has a refractive index below 1.40.

12. The coated photonic crystal fiber of claim 1, wherein said protective coating has a refractive index below 1.37.

13. The coated photonic crystal fiber of claim 1, wherein said protective coating is obtained by curing a resin composition.

14. The coated photonic crystal fiber of claim 13, wherein said curing is effected by ultraviolet radiation.

15. The coated photonic crystal fiber of claim 13, wherein said curing is effected by electron beam radiation.

16. The coated photonic crystal fiber of claim 13, wherein said curing is effected by heat.

17. The coated photonic crystal fiber of claim 1, wherein said protective coating has a glass transition temperature of at most 10° C.

18. The coated photonic crystal fiber of claim 1, wherein said coated photonic crystal fiber comprises a further coating surrounding said protective coating.

19. The coated photonic crystal fiber of claim 18, wherein said further coating has a glass transition temperature of at least 40° C.

20. The coated photonic crystal fiber of claim 18, wherein said further coating has a secant modulus of at least 300 MPa.

21. The coated photonic crystal fiber of claim 18, wherein said protective coating and/or said further coating is obtained by curing a composition comprising an oligomer having at least one ethylenically unsaturated group.

22. The coated photonic crystal fiber of claim 21, wherein said oligomer comprises a backbone having ether and/or ester groups.

23. The coated photonic crystal fiber of claim 21, wherein said oligomer comprises fluorine atoms.

24. The coated photonic crystal fiber of claim 1, wherein said protective coating is obtained by curing a composition comprising at least one silane coupling agent.

25. The coated photonic crystal fiber of claim 18, wherein said protective coating and/or said further coating are obtained by curing a composition comprising at least one photoinitiator.

* * * * *